United States Patent [19]

Franco-Vila

[11] 4,177,796
[45] Dec. 11, 1979

[54] MAGNETIC THERMAL VIBRATIONAL DEVICE FOR THE TREATMENT OF ARTHRITIS AND THE LIKE

[76] Inventor: Jose J. Franco-Vila, 730 E. 6th Pl., Hialeah, Fla. 33010

[21] Appl. No.: 826,410

[22] Filed: Aug. 22, 1977

[51] Int. Cl.² .................. A61N 1/42; A61H 23/00
[52] U.S. Cl. .................. 128/1.5; 128/24.2; 128/41; 128/399
[58] Field of Search .................. 128/1.3–1.5, 128/24.1, 24.2, 41, 362, 399, 405

[56] References Cited

U.S. PATENT DOCUMENTS

| | | | |
|---|---|---|---|
| 1,634,373 | 7/1927 | Mann | 128/1.5 |
| 2,766,750 | 10/1956 | Darcissac | 128/24.2 |
| 3,633,570 | 1/1972 | DeAngeli | 128/41 |
| 3,658,051 | 4/1972 | MacLean | 128/1.5 |

FOREIGN PATENT DOCUMENTS

| | | | |
|---|---|---|---|
| 1233094 | 1/1967 | Fed. Rep. of Germany | 128/24.2 |
| 185284 | 9/1922 | United Kingdom | 128/41 |

OTHER PUBLICATIONS

Bennett, "Magnetism...", pp. 21-32, 1906.

*Primary Examiner*—Lee S. Cohen
*Attorney, Agent, or Firm*—Barry L. Haley; Eugene F. Malin

[57] ABSTRACT

A device for simultaneously applying electromagnetic alternating directional energy, thermal, and vibrational energy to various areas of the body which has been found to reduce or even eliminate the pains and symptoms caused from arthritis, bursitis and other bone joint maladies. The device includes a housing, an electromagnet disposed in said housing, an elastic band having a pair of permanent magnets coupled magnetically on each side of the band to each other with the elastic band being suspended at each end to the housing and positioned within the alternating magnetic field of the electromagnet. The electromagnet has a shaped steel core which acts to concentrate the magnetic flux lines through the suspended permanent magnets and is driven by low frequency alternating current causing the suspended magnets to vibrate. The electromagnet core is contructed in such a way to contribute heat for thermal application to the body simultaneously in conjunction with the concentrated magnetic field and vibration. The resulting simultaneous effects of the low frequency alternating (in direction) magnetic field, the vibrating elastic band and thermal concentration of energy is found to be extremely effective for the reduction or elimination of pain and other body disorders caused by arthritis, bursitis and other related bone joint diseases.

3 Claims, 4 Drawing Figures

MAGNETIC THERMAL VIBRATIONAL DEVICE FOR THE TREATMENT OF ARTHRITIS AND THE LIKE

BACKGROUND OF THE INVENTION

This invention relates generally to a therapeutic device for reducing periodically or eliminating the deleterious effects caused from bone joint diseases such as arthritis, bursitis and the like, and specifically to a therapeutic device which provides for the application of concentrated alternating electromagnetic energy, mechanical vibrational energy, and thermal energy to a localized area of the body such as bone joints of a hand, arm and the like.

The use of electromagnetic energy and magnetic energy alone as a therapeutic aid for various types of diseases occuring to various mammals is well known in the prior art. A vast spectrum of various diseases has been purported to be reduced or totally eliminated by several of these devices. In U.S. Pat. No. 3,658,051, issued to MacLean, a method of treating living things using high intensity pulsating magnetic fields is shown. The method is alleged to be effective for curing a plethora of varying diseases by applying a unidirectional pulsed magnetic field to the particular part of the body that is ailing. In the instant invention, Applicant has discovered that the application simultaneously of concentrated, magnetic field energy which is alternating in direction at a low frequency in combination with mechanical vibration which vibrates the joint area and heat application to the body will reduce the symptomatic effects of arthritis, rheumatism, rheumatoid-arthritis, osteoarthritis, radiohumeral bursitis, and other similar disorders related to the musculoskeletal and connective tissues.

The device includes an electromagnet having a core which is designed to intensify the flux lines by concentrating them into a central supporting area which has connected thereacross an elasticized band having a pair of ceramic permanent magnets, one on each side of the band supporting therein. An alternating current applied to the coil of the electromagnet generates an alternating magnetic field that vibrates the permanent magnets, producing mechanical vibration across the elastic band which can be utilized to engage the skin area surrounding the particular joint or tissue being subjected to the intensified field. Furthermore, heat is generated by the electromagnetic field in combination with the core due to hysterisis caused by the alternating magnetic field.

The instant invention has been applied to several patients and the results have demonstratively shown the effectiveness of the device. In specific cases, long time sufferers of severe arthritis and vertebrae problems have recovered for periods of months with periodic treatment.

BRIEF DESCRIPTION OF THE INVENTION

A method and apparatus for reducing or curing the effects of arthritis, rheumatism and other muscular skeleton connective joint diseases and disorders involves applying concentrated magnetic field energy which is alternating in direction at a low frequency in combination with mechanical vibrations and thermal energy to particular parts of the human body which are affected by such a disease.

In one embodiment, the apparatus is constructed of an electromagnet made of several sheets of silicon steel which are shaped at two ends to direct the flux lines of force of the magnetic field between the end faces of the electromagnet. A housing into which the electromagnet is placed includes supporting walls to which is connected an elastic band that is disposed in the same plane as the open end faces of the electromagnet. Disposed on each side of said elastic band are two permanent magnets which have their north-south axes perpendicular to the elastic band which allows them to be joined and held together by the attractive force of the magnets.

The magnets themselves may be covered with a soft material to allow comfortable contact with the body skin or a resilient shield may be placed across the entire housing covering the flexible band and permanent magnets.

Heating for the body area results from the enclosure of the electromagnet's coil in the housing that thermally heats the cover which is resilient or the elasticized band and magnets themselves.

Mechanical vibration is achieved by placing the magnetic axis of the two permanent magnets across the elastic band perpendicular to the flux lines of the electromagnet. By applying alternating current and varying the direction of the magnetic field at a low frequency, the permanent magnets coupled across the elastic band vibrate perpendicularly in the alternating magnetic field setting up a mechanical vibrational pattern which is used as part of the therapy in accordance with the invention.

In accordance with the tests that have been successfully achieved in using the invention, the invention has been applied to various areas of the body of a person having arthritis, rheumatiod arthritis, and to the areas such as the bone joints or other surrounding tissue, with the device being applied for time periods between thirty minutes up to an hour at a particular time.

The medical physiological and biological explanation of what effects the alternating magnetic fields have, especially in conjunction with the mechanical vibrations and the thermal application are not clearly understood, although I strongly believe it reactivates blood circulation due to the electrolitic composition of the former. As one possible explanation, it is believed that perhaps the alternating electromagnetic flux penetrating back and forth through the bone joints and tissues have the property of destroying or eliminating the crystals of calcium phosphates created by the arthritic or rheumatic conditions and at the same time to reactivate blood circulation due to the electrolitic composition of the former.

It is an object of this invention to provide an improved therapeutic device for reducing or curing the symptomatic effects of diseases such as arthritis, rheumatism, rheumatoid arthritis, osteoarthritis, radiohumeral bursitis and like related bone diseases by the application of an alternating highly concentrated magnetic field to the particular diseased area of the body.

It is another object of this invention to provide an improved therapeutic device for the elimination of bone joint diseases such as arthritis or rheumatism through the application of an alternating magnetic field in combination with the simultaneous application of mechanical vibration and thermal stimulation to a particular area of the body.

But yet still another object of this invention is to provide a non-complex therapeutic device which is readily constructed at reduced cost and which can be successfully useful in the treatment of arthritis, rheumatism or other bone joints disorders.

And yet still another object of this invention is to provide a relatively portable therapeutic device for the treatment of arthritis or rheumatism that can be administered by the user at home without the necessity of providing supervision of a doctor for the treatment of certain bone joint disorders.

In accordance with these and other objects which will be apparent hereinafter, the instant invention will now be described with particular reference to the accompanying drawings.

PREFERRED EMBODIMENT OF THE INVENTION

Figure 1:
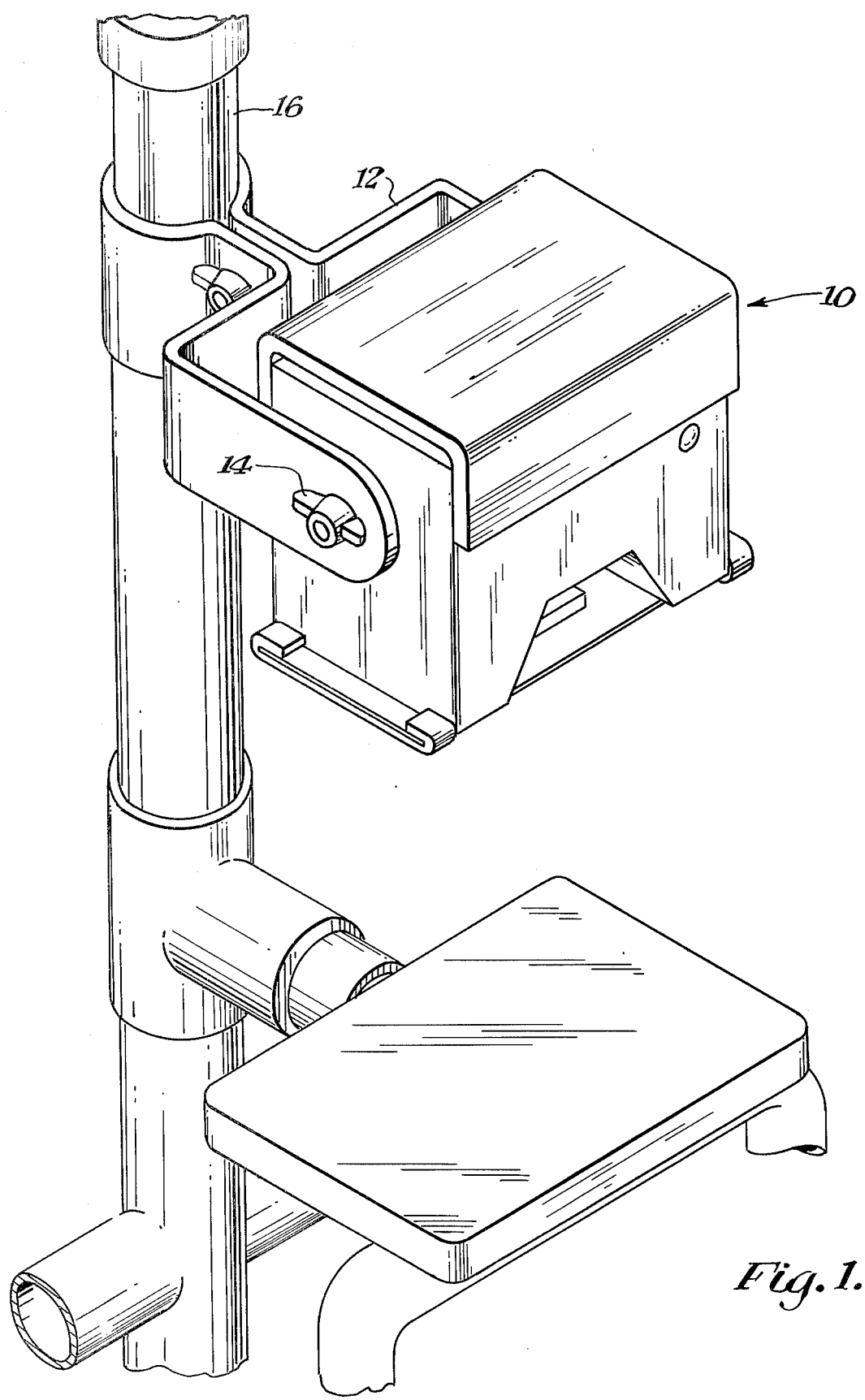
FIG. 1 shows the perspective view of the instant invention coupled to a supporting device and a mounting moveable bracket.

Referring now to the drawings, and specifically FIG. 1, the instant invention is shown generally at 10 mounted on a bracket 12 pivotally by threaded pins (not shown) and wing nuts 14, the bracket itself being moveably mounted on a supporting pipe or pole 16. With this installation the device 10 may be adjusted and moved so that a particular fixed position can be achieved relative to the patient.

Figure 2:
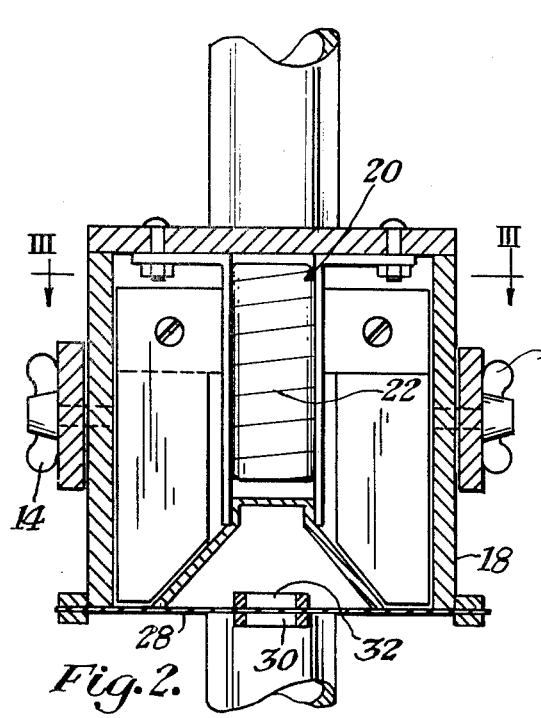
FIG. 2 shows a side elevational view partially in cross-section of the instant invention.
Figure 3:
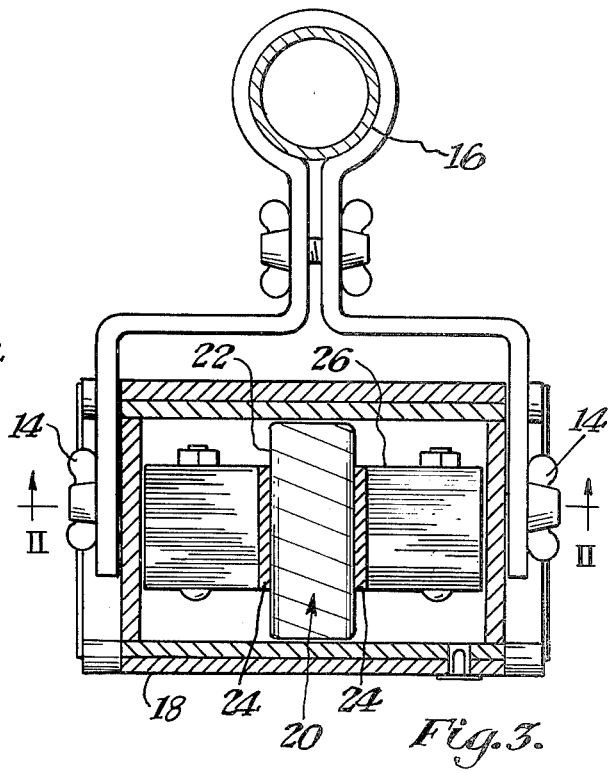
FIG. 3 shows a top plan view of the instant invention.
Figure 4:
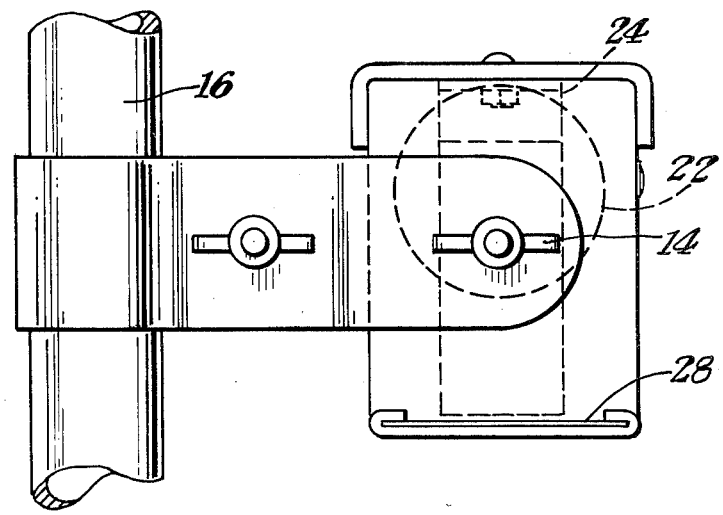
FIG. 4 shows a side elevational view of the instant invention.

FIGS. 2, 3 and 4 show the device which includes a housing 18 into which an electromagnet 20 is disposed, the electromagnet including a coil 22 and tapered steel plates 24 which have flat end faces 26 which act to concentrate the flux lines produced by the coil of the electromagnet in combination with the magnetization of the steel plates. Stretched across between the housing walls is an elastic band 28 which has a pair of permanent magnets 30 and 32 coupled thereacross. The permanent magnets 30 and 32 have their north south axes perpendicular to the elastic band and as such are positioned so that one pole of magnet 32 attracts the opposite pole of magnet 30 firmly coupling the magnets (with the elastic disposed between) to the band. The elastic band 28 is arranged and coupled to the housing such that the plane of the band is parallel and co-planar with the end faces of the magnet end faces. Thus the permanent magnets suspended on the band are disposed within the concentrated flux field of the electromagnet and with the orientation of the permanent magnet axis of each magnet, the magnetic axes (being perpendicular to the elastic band) cause both magnets 30 and 32 to vibrate rapidly when an alternating magnetic field is generated by the electromagnet when it is alternated at a low frequency. Heat is generated by the hysterisis created within the steel plates of the electromagnet and is thus trapped within the housing, warming the end face area also. An additional end face may be made of a very resilient material such as rubber and placed over the elastic band and the permanent magnets, further trapping heat within the device which will warm the area for applying heat to the body.

In one embodiment of the invention that was utilized for treating patients, an electromagnetic device having 85,000 lines of force per square inch was used that is constructed of seventy two sheets of silicone steel of 0.028 thickness each having a magnetic permeability of 1500 and a magnetizing force of 19 ampere-turns per inch. The electromagnetic coil is donut-shaped and was wound using 11,000 turns of plain enameled No. 19 copper wire having 1288 circular mils and a resistance of 8.21 ohms per 1,000 feet. The power source used on the electromagnet is 110 Volt AC conventional household current. For additional strength a condenser may be coupled to the circuit of the electromagnetic for boosting the magnetic energy of the device. The steel core has intentionally induced hysteris effects from the electromagnet which results in the production of heat which is applied simultaneously with the magnetic field and the vibrating magnets of the device.

EXAMPLE I

A female patient of 65 years of age was treated with one embodiment of the invention on the right hand, the right hand being completely unable to be closed prior to the therapeutic stimulation. The fingers on the hand had lost normal movement and flexibility due to arthritis. The device was utilized and the hand was treated one hour per day, three days a week over a three week period. At the end of the three week period, the hand experienced normal movement and flexibility to almost 100 percent of normal.

Additional tests have been run on additional patients with control conditions such that the patient was not aware of whether or not the electromagnetic field was in fact turned on. The tests clearly show improved results for arthritic rheumatory joint disorders with the magnetic field applied and without the magnetic field no improved results were achieved.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A therapeutic device for treating arthritis, rheumatism, or other similarly related bone joint diseases, comprising:
   an electromagnet, including a coil, said electromagnet having shaped, spaced apart end faces providing a concentrated field of magnetic energy;
   an AC power source connected to said electromagnet for alternately magnetizing said coil;
   an elastic supporting band positioned across said spaced apart end faces of said electromagnet;
   at least one permanent magnet connected to said elastic supporting band, suspended between the electromagnet end faces, said suspended permanent magnet having its magnetic axis oriented perpendicular to the magnetic field of said electromagnet;
   said electromagnet including steel plates coupled together to produce hysterisis;
   a housing enclosing said electromagnet for entrapping heat within said housing; and
   said elastic supporting band connected at opposite ends to said housing forming a resilient closure for said housing whereby said resilient closure may contact the skin of a patient to produce thermal vibrational effects while an alternating magnetic field is simultaneously disposed therethrough.

2. The method of treating of human being suffering from rheumatism, arthritis or other related bone joint diseases comprising the steps of:
 (a) applying for one hour periods an alternating magnetic field to the body area having the disorder, said alternating field being of 60 cycles per second and 85,000 lines of force per square inch;
 (b) simultaneously mechanically vibrating the same body area.

3. The method, as in claim 2, including the step of:
 (c) applying simultaneously thermal energy to the same body area.

* * * * *